United States Patent [19]

Lukacs, III

[11] Patent Number: 4,874,828

[45] Date of Patent: Oct. 17, 1989

[54] HEAT RESISTANT THERMOSETTING PHOSPHAZENE-IMIDE COPOLYMERS

[75] Inventor: Alexander Lukacs, III, Wilmington, Del.

[73] Assignee: Hercules Incorporated, Wilmington, Del.

[21] Appl. No.: 104,150

[22] Filed: Oct. 1, 1987

[51] Int. Cl.$^4$ .............................................. C08F 222/40
[52] U.S. Cl. .................................... 526/262; 526/275; 526/276; 528/399
[58] Field of Search .................. 526/262, 275, 276; 528/399

[56] References Cited

U.S. PATENT DOCUMENTS

| | | | |
|---|---|---|---|
| 4,107,146 | 8/1978 | Dieck et al. | 528/399 |
| 4,145,479 | 3/1979 | Adams et al. | 428/500 |
| 4,518,754 | 5/1985 | Locatelli et al. | 526/262 |
| 4,550,177 | 10/1985 | Kumar et al. | 548/413 |
| 4,568,498 | 2/1986 | Allen et al. | 260/927 |
| 4,579,880 | 4/1986 | Ohashi et al. | 526/276 |
| 4,602,048 | 6/1986 | Penton et al. | 521/82 |
| 4,743,647 | 5/1988 | Domeier | 526/262 |

*Primary Examiner*—Briggs, Sr., Wilbert J.
*Attorney, Agent, or Firm*—Mark Goldberg; William S. Alexander

[57] ABSTRACT

Novel thermoset polymers are prepared by reacting an allyl or vinyl aryl or aryloxy substituted cyclophosphazene with a bis-maleimide.

4 Claims, No Drawings

HEAT RESISTANT THERMOSETTING PHOSPHAZENE-IMIDE COPOLYMERS

This invention relates to new cyclophosphazene-based thermoset resins. More specifically, it relates to such resins which are superior reaction proiducts of vinyl or allyl substituted cyclophosphazenes with suitable bis-maleimides.

There is a current need in several industries and, in particular, in the aerospace industry, for high performance structural plastics materials capable of withstanding high temperatures. The need is not only for materials which do not contribute to the spread of flames, but also for materials which do not decompose by mechanisms which generate toxic volatiles.

In accordance with this invention, a thermoset resin having such properties is provided which is a reaction product of an aryl or aryloxy substituted cyclophosphazene wherein an average of at least two aryl or aryloxy grouips are substituted with an allyl or vinyl group, and a bis-maleimide-based dienophile.

The cyclophosphazene component of the resins of this invention has the general formula:

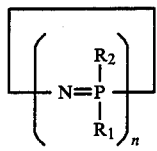

wherein n is 3 or 4 and $R_1$ and $R_2$ are the same or different, many vary from one phosphorus atom to the next on the same cyclophosphazene ring and are selected from the group consisting of:

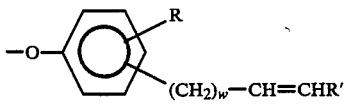 (a)

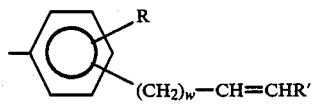 (b)

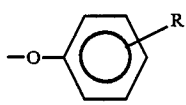 (c)

and

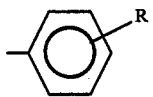 (d)

where w=0 or 1, and R and R' are selected from the group consisting of H or a nonreactive moiety. The average degree of substitution per cyclophosphazene ring by $R_1$ and $R_2$ radicals selected from the group consisting of:

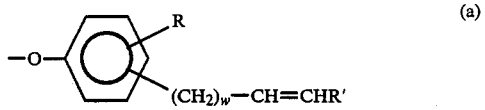 (a)

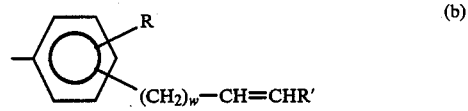 (b)

must be at least two.

The term nonreactive moiety refers to any substituent on the benzene ring that does not take part in a subsequent thermal polymerization and curing reaction. Such substituents for R, for example, include hydrogen, halogen, nitro, $C_1$ to $C_{12}$ carbon oxyalkyl, cyano, amino, $C_1$ to $C_{12}$ carbon N-alkyl or N-dialkyl, N-aryl, $C_1$ to $C_{12}$ carbon alkyl, $C_1$ to $C_{12}$ carbon haloalkyl, aryl, or oxyaryl. Such substituents for R', for example, include hydrogen, halogen, $C_1$ to $C_{12}$ carbon alkyl, $C_1$ to $C_{12}$ carbon haloalkyl, and aryl.

Mixtures of the cyclotriphosphazene derivative and the analogous cyclotriphosphazene derivative can also be used. In most cases, in fact, the named cyclophosphazene will contain a small amount of other cyclophosphazenes, i.e., the tetracyclophosphazene will contain at least a small amount of the tricyclophosphazene and vice versa. Additionally, small amounts of higher, i.e., $C_5$ to $C_{12}$ and linear phosphazenes, are usually present as by-products of the cyclization procedures.

Typical cyclophosphazene derivatives suitable for use in the resins of this invention include, e.g.:
2,4,6,6-tetraphenoxy-2,4-dieugenoxy cyclotriphosphazene; hexakis(eugenoxy) cyclotriphosphazene;
2,4,6,6-tetraphenyl-2,4-dieugenoxy cyclotriphosphazene; hexakis(isoeugenoxy)cyclotriphosphazene;
2,4,6,6,8,8-hexaphenoxy-2,4-diisoeugenoxy cyclotriphosphazene; and
2,2,4,4-tetraphenyl-6,6-diallylphenoxy cyclotriphosphazene.

Specific examples of polyfunctional maleimide compounds suitable for use in this invention include:
N,N'-4,4'-diphenylmethane-bis-maleimide;
N,N'-ethylene-bis-maleimide;
N,N'-ethylene-bis(2-methylmaleimide);
N,N'-trimethylene-bis-maleimide;
N,N'-tetramethylene-bis-maleimide;
N,N'-hexamethylene-bis-maleimide;
N,N'-1,4,-cyclohexylene-bis-maleimide;
N,N'-meta-phenylene-bis-maleimide;
N,N'-para-phenylene-bis-maleimide;
N,N'-2,4-toluene-bis-maleimide;
N,N'-2,6-toluene-bis-maleimide;
N,N'-4,4'-diphenylmethane-bis-maleimide;
N,N'-4,4'-3,3'-dichloro-diphenylmethane-bis-maleimide;
N,N'-4,4'-diphenyl-ether-bis-maleimide;
N,N'-4,4'-diphenylsuphone-bis-maleimide;
N,N'-4,4'-dicyclohexylmethane-bis-maleimide;
N,N'-α, α'-4,4'-dimethylenecyclohexane-bis-maleimide;
N,N'-meta-xylene-bis-maleimide;
N,N'-para-xylene-bis-maleimide;
N,N'-4,4'-diphenyl-cyclohexane-bis-maleimide;
N,N'-meta-phenylene-bis-tetrahydrophthalimide;
N,N'-4,4'-diphenylmethane-bis-citraconimide;
N,N'-4,4'-2,2-diphenylpropane-bis-maleimide;

N,N'-4,4-1,1-diphenyl-propane-bis-maleimide;
N,N'-4,4'-triphenylmethane-bis-maleimide;
N,N'-α, α'-1,3-dipropylene-5,5-dimethyl-hydantoin-bis-maleimide;
N,N'-4,4'-(1,1,1-triphenyl ethane)-bis-maleimide;
N,N'-3,5-triazole-1,2,4-bis-maleimide;
N,N'-4,4'-diphenyl-methane-bis-itaconimide;
N,N'-para-phenylene-bis-itaconimide;
N,N'-4,4'-diphenylmethane-bis-dimethyl-maleimide;
N,N'-4,4'-2,2-diphenylpropane-bis-dimethylmaleimide;
N,N'-hexamethylene-bis-dimethyl-maleimide;
N,N'-4,4'-(diphenyl ether)-bis-dimethyl-maleimide;
N,N'-4,4'-diphenylsulphone-bis-dimethylmaleimide;
N,N'-(oxydi-para-phenylene)-bis-maleimide;
N,N'-(oxydi-para-phenylene)-bis-(2-methyl-maleimide);
N,N'-(methylenedi-para-phenylene)bis-maleimide;
N,N'-(methylenedi-para-phenylene)bis-(2-methylmaleimide);
N,N'-(methylenedi-para-phenylene)bis(2-phenylmaleimide);
N,N'-(sulfonyldi-para-phenylene)bis-maleimide;
N,N'-(thiodi-para-phenylene)bis-maleimide;
N,N'-(dithiodi-para-phenylene)bis-maleimide;
N,N'-(sulfonyldi-meta-phenylene)bis-maleimide;
N,N'-(ortho, para-isopropylidenediphenylene)bis-maleimide;
N,N'-(isopropylidenedi-para-phenylene)bis-maleimide;
N,N'-(ortho,para-cyclohexylidenediphenylene)bis-maleimide;
N,N'-(cyclohexylidendi-para-phenylene)bis-maleimide;
N,N'-(ethylenedi-para-phenylene)bis-maleimide;
N,N'-(4,4''-para-triphenylene)bis-maleimide;
N,N'-(para-phenylenedioxydi-para-phenylene)bis-maleimide;
N,N'-(methylenedi-para-phenylene)bis-(2,3,-dichloromaleimide); and
N,N'-(oxydi-para-phenylene)bis(2-chloromaleimide).

The thermosettable resin compositions of this invention, of course, can comprise more than one type of polyfunctional maleimide compound as set forth above, and may comprise a mixture of several such compounds. It is preferable, however, to use N,N'-4,4'-diphenyl-methane-bis-maleimide.

To prepare the thermoset resin of this invention, the cyclophosphazene containing at least two vinyl or allyl substituted phenolic groups is simply mixed with the bismaleimide. The reaction takes place without benefit of any catalyst other than heat, which determines the rate. The precise time and temperature required will depend upon the cyclophosphazene and bis-maleimide combination employed. A temperature of about 150° to 300° C. and, more preferably, about 170° to 250° C. is preferred. In many cases a two stage heating is carried out, e.g., 2 hours at 170° C. followed by 2 to 6 hours at 240° C.

The aryl or aryloxy substituted cyclophosphazenes suitable for use in preparation of the thermoset polymers of this invention are prepared by complete or partial replacement of the halogen of a halocyclophosphazene by the appropriate allyl or vinyl substituted phenyl or phenoxy residue. An average of at least two and preferably at least three of the halogens must be replaced by allyl or vinyl substituted phenyl or phenoxy residues. The remainder can be either unsubstituted (i.e., halogen not replaced) or substituted by suitable unreactive residues (preferably aryl or aryloxy).

To attach a phenyl radical directly onto the cyclophosphazene ring (i.e., via a carbon to phosphorus bond), the cyclophosphazene can be refluxed in benzene in the presence of AlCl₃ and triethylamine. This procedure is reported by Shaw et al J. Chemical Society 131 (1964).

Phenoxy radicals are typically attached to the cyclophosphazene ring via the appropriate sodium phenoxide salt. The phenoxide salt is refluxed with the cyclophosphazene in a suitable solvent for the appropriate time. This procedure is reported, for example, by McBee et al 5(3) Inorganic Chemistry 450 (1966). Either a substituted or an unsubstituted phenoxy group can be attached via this technique.

As stated hereinbefore, the polymerization reaction can take place at temperatures between 150° C. and about 300° C. Due to the crosslinked thermoset nature of the polymer, polymerization is carried out in a mold to form the desired shape directly. Polymerization is believed to take place primarily via a Diels-Alder cycloaddition-type reaction wherein the >C=C< grouping of the bis-maleimide cyclizes with the vinyl or allyl group. A large fraction of the resulting structure is thus believed to be the following:

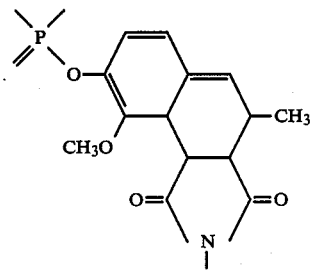

when a vinyl phenoxy substituted cyclophosphazene is used, e.g., an iso eugenoxy substituted cyclophosphazene. Alternatively, a free radical cure may be involved, or, more likely, a combination of the two mechanisms.

Crosslinked, thermoset polymers, according to the invention, are characterized by excellent high temperature properties. They exhibit very high glass transition temperature (Tg), typically on the order of 300° C. and higher as measured by the DMA (dynamic mechanical analysis) technique. Concomitant with high Tg is a very low thermal expansion coefficient of no more than about $80 \times 10^{-6\circ}$ C. in most cases. This combination of properties makes these polymers useful in electronic applications, in particular, in high performance circuit boards where ambient heat can be a harmful factor with other circuit board construction materials.

The novel polymers of this invention also exhibit a high degree of oxidative stability. Thermal decomposition does not begin until temperatures in the vicinity of 350° C. are reached. At 650° C. a residue of 50% is obtained in air. They are likewise flame retardant and when exposed to direct flame, they do not emit toxic fumes. These properties make the polymers useful in a number of structural applications where flame retardant ablative properties are required. Flammability is proportional to number of crosslinking sites on the phosphazene, e.g., the polymer of the hexasubstituted phosphazene and bis-maleimide does not burn.

Depending upon a particular application, any of the thermosettable resin compositions of this invention can be admixed with one or more additional components to modify the properties of the cured resin end product, provided that such additives do not adversely affect cure. Examples of such components include inorganic fillers such as silica, silica glass, clay, aluminum hydroxide, asbestos, mica, gypsum, kaolin, cement, talc, calcium carbonate and the like. In similar fashion, catalysts, stabilizers, free radical initiators, tackifiers, antioxidants, plasticizers, pigments, dyestuffs, mold release agents and flame retardant compounds, may be added to the thermosettable resin compositions of this invention. Still further, other components which can be added to the resin compositions of this invention to optimize said resins for various end uses include reactive rubbers and thermoplastics.

The invention is illustrated by the following examples, wherein parts are parts by weight, unless otherwise indicated.

EXAMPLE 1

A. Preparation of 2,2-diphenyl-4,6-diphenoxy-4,6-dieugenoxy-cyclotriphosphazene A suspension of aluminum chloride (466.7 parts) in benzene (440 parts) was stirred in an ice bath. To this suspension was added a solution of triethylamine (130 parts) and benzene (440 parts), dropwise over a two hour period. The entire reaction was performed under a nitrogen atmosphere. The light brown solution was stirred in the ice bath for 1 hour, after which time cyclotriphosphazene chloride (150 parts) was added. The resulting light brown solution was then refluxed under nitrogen for six days.

After the reflux time was complete, the resulting black solution was cooled to room temperature and then added slowly to a cold solution of 2N hydrochloric acid. The benzene layer was separated, dried over sodium sulfate and stripped of solvent, resulting in a clear brown liquid. Vacuum sublimation at 100° C. yielded a dark brown solid (151.5 parts). The white solid material (9.6 g) that sublimed was found to be unreacted cyclotriphosphazene chloride. The dark brown solid product was 4,4-diphenyl-2,2,6,6-tetrachlorocyclotriphosphazene in 81.6% yield according to elemental and NMR analysis.

| Analysis | % C | % H | % N |
|---|---|---|---|
| Found (HPLC) | 31.9 | 2.21 | 9.83 |
| Calculated | 33.4 | 2.32 | 9.75 |

$1_H$ NMR 90 MHZ(acetone $d_6$) $\delta$8.80-6.8(unresolved phenyl).
$^{31}$P NMR 146 MHZ(acetone) $\delta$21.3(t),$\delta$18.4(d).

To a chilled (ice bath) solution of phenol (56.44 parts) and acetone (800 mls), was added sodium hydride (24 parts) over a two hour period. The resulting brown sodium phenoxide solution was stirred for thirty minutes. To this solution was added a solution of the previously prepared diphenyltetrachlorocyclotriphosphazene (125 parts) and acetone (700 mls). The resulting, milky white solution was refluxed under nitrogen for six days.

After the reflux time was complete, the solution was cooled to room temperature and stripped of solvent. The resulting brown oil was extracted with a solution of ether and water (1:1). The brown ether layer was separated and washed once with water, and passed through a short column of acidic alumina. The ether filtrate was dried over sodium sulfate, filtered and concentrated to about half its volume. The solution was then refrigerated overnight, at which time an off-white solid had crystallized. The solid was filtered and air dried. The ether filtrate was concentrated further and again refrigerated overnight, at which time more of the off-white solid crystallized. The solid was filtered and air dried. The ether filtrate was concentrated further and again refrigerated overnight. Another portion of the solid was recovered and mixed with the first portion. A total of 39.5 parts of the off-white solid was recovered (25% yield). This solid was 4,4-diphenyl-2,6-diphenoxy-2,6-dichlorocyclotriphosphazene.

A sodium eugenoxide solution was prepared by adding sodium hydride (1.5 parts) to a chilled solution of eugenol (6.08 parts) and acetone (100 mls). To this solution was added a solution of the diphenyl-diphenoxy-dichlorocyclotriphosphazene (10.0 parts) and acetone (100 mls). The resulting yellow solution was then refluxed, under nitrogen, for forty-eight hours.

After this time the reaction mixture was cooled, centrifuged and the supernatant stripped of solvent. The dark, orange residue was then dissolved in ether and the solution was washed with water. The ether layer was separated, dried over sodium sulfate, filtered and stripped of solvent. The resulting brown oil was washed with cyclohexane. The cyclohexane solution was decanted off and stripped of solvent, resulting in a light brown oil. The oil was heated under vacuum (180° C.) to remove residual solvent. A very viscous, clear, light brown oil was recovered. The product was 4,4-diphenyl-2,6-diphenoxy-2,6-dieugenoxycyclotriphosphazene.

| Analysis | % C | % H | % N |
|---|---|---|---|
| Found (HPLC) | 64.41 | 5.21 | 5.44 |
| Calculated | 64.44 | 5.24 | 5.24 |

$1_H$ NMR 90 MHZ(acetone $d_6$) $\delta$7.4-6.2(unresolved phenyl, $\delta$26H), $\delta$5.8(complex vinyl multiplet, 2H), $\delta$5.0(vinyl multiplet, 4H), $\delta$3.6(methyl s, 6H), $\delta$3.2(methylene, 4H).
$^{31}$P NMR 146 MHZ(acetone) $\delta$22.2(t), $\delta$9.3(d).

B. Polymerization of 4,4-diphenyl-2,6-diphenoxy-2,6-dieugenoxy cyclotriphosphazene The named compound (1.01 parts) was ground together with 0.45 part methylene dianiline bis-maleimide. The mixture was placed into an aluminum pan, heated to 170° C. for two hours. The temperature was then raised to 220° C. for two hours. A clear brown solid polymer was recovered.

Tg of this polymer by the DSC method at 10° C. per minute heating rate in nitrogen was greater than 260° C. Upon heating at 20° C. per minute, the residue at 900° C. was 4.27% in air and 33.87% in nitrogen. Onset of degradation occurred at about 350° C. in air and about 360° C. in nitrogen.

EXAMPLE 2

A. Preparation of Hexakis(Eugenoxy) Cyclotriphosphazene

To a chilled solution of eugenol (246.9 parts) in acetone (600 mls) was added (very slowly) sodium hydride (104 parts).

To the resulting yellow solution was added a solution of the cyclotriphosphazene chloride (150 parts) and acetone (400 mls). The brown solution was then refluxed under nitrogen for 60 hours, during which time the solution turned a tan color. After the reaction was complete, the mixture was cooled and centrifuged, and the liquid was stripped of solvent. The resulting light brown liquid was poured into rapidly stirred, distilled water (1 liter). After a short time a white solid precipitate formed. This mixture was agitated in a Waring blender to facilitate solids washing. The solid was then filtered, washed with water, methanol and, finally, pentane.

After drying overnight at 40° C. under vacuum, 407 parts of white powder was recovered (85% yield).

| | Analysis | | |
|---|---|---|---|
| | % C | % H | % N |
| Found (HPLC) | 64.57 | 5.92 | 3.77 |
| Calculated | 64.68 | 5.92 | 3.51 |
| $1_H$ NMR 90 MHZ(acetone $d_6$) $\delta$7.0(d, J = 3HZ, 6H), $\delta$6.7(s, 6H), $\delta$6.5(d, J = 3HZ, 6H), $\delta$5.9(complex phenyl multiplet, 6H), $\delta$5.0(apparent vinyl multiplet, 12H), $\delta$3.6(methyl s, 18H), $\delta$3.2(methylene d, 12H). | | | |
| $^{31}$P NMR 146 MHZ(acetone) $\delta$10.8(s). | | | |

B. Polymerization of Hexakis(Eugenoxy) Cyclotriphosphazene

To 9.42 parts of the named compound was added 3.03 parts methylene dianiline bis-maleimide. These were ground to a fine powder. The powder was placed into an aluminum pan and heated to 170° C. over a two hour period. At the end of the two hour period, the temperature was increased to 220° C. and held for two hours. A clear light brown polymer was recovered.

Tg of the polymer by DSC method at 10° C. per minute heating rate in nitrogen was greater than 260° C. Upon heating at 20° C. per minute, the residue at 900° C. was 10.48% in air and 42.81% in nitrogen. Onset of degradation occurred at about 400° C. in both air and nitrogen.

EXAMPLE 3

A. Preparation of Tris(Eugenoxy) Tris(Phenoxy) Cyclotriphosphazene

Sodium eugenoxide was prepared by slowly adding sodium hydride (3.80 parts) to a solution of eugenol (15.6 parts) and acetone (150 mls, chilled). To this solution was added a solution of cyclotriphosphazene chloride (10 parts) and acetone (100 mls). The resulting mixture was then refluxed under nitrogen overnight.

Sodium phenoxide was prepared by slowly adding sodium hydride (3.80 parts) to a chilled solution of phenol (8.93 parts) and acetone (150 mls). This solution was then added to the reaction mixture, and reflux conditions were maintained for forty-eight hours.

After this time, the mixture was cooled, centrifuged and stripped of solvent. The brown, oily residue was then washed with several quantities of water and a creamy, white material which was recovered was then stirred in hexane. A light brown oil remained. The oil was dissolved in ether and passed through an alumina column. The solvent was dried over sodium sulfate and stripped to yield a very viscous brown oil (13.19 parts). The oil was heated to distill any impurities (180° C. under vacuum), giving the solid product in 50% yield.

| | Analysis | | |
|---|---|---|---|
| | % C | % H | % N |
| Found (HPLC) | 62.76 | 5.35 | 4.45 |
| Calculated | 63.81 | 5.31 | 4.65 |
| $1_H$ NMR 90 MHZ(acetone $d_6$) $\delta$7.1-6.3(complex phenyl multiplet, 24H), $\delta$5.9(complex vinyl multiplet, 3H), $\delta$5.0(apparent vinyl triplet, 6H), $\delta$3.2(methylene d, 6H). | | | |
| $^{31}$P NMR 146 MHZ(acetone) $\delta$10.5(s). | | | |

B. Polymerization of Tris(eugenoxy) Tris(phenoxy)cyclotriphosphazene

The named compound (1.59 parts) and methylene dianiline bis-maleimide (0.63 parts) were ground together to a fine powder. The mixture was placed in an aluminum pan and heated to 170° C. At the end of two hours, the temperature was increased to 220° C. and held at that point for an additional two hours. A dark brown polymer was recovered.

Tg of this polymer by the DSC method at 10° C. per minute heating rate in nitrogen was greater than 260° C. Upon heating at 20° C. per minute, the residue at 900° C. was 9.35% in air and 41.51% in nitrogen. Onset of degradation occurred at about 335° C. in air and 360° C. in nitrogen.

EXAMPLE 4

A. Preparation Of Hexakis(isoeugenoxy)cyclotriphosphazene (X25890-71)

Sodium hydride (20.0 g of 60% slurry in mineral oil, 0.50 mol) was added to a solution of isoeugenol (82.1 g, 0.50 mol) in acetone (700 mls) which was chilled to ice bath temperature. After 30 minutes hexachlorocyclotriphosphazene (25.0 g, 0.072 mol) was added and the resulting solution refluxed under nitrogen for 60 hours. After the reaction was complete, the mixture was cooled to room temperature, centrifuged, and the liquid phase was stripped of solvent to yield a brown oil. The oil was poured into rapidly stirred, distilled water (1 liter). After a short time, a white precipitate formed. This mixture was agitated in a Waring blender to facilitate solids washing. The solids were then filtered, washed with water, methanol and, finally, pentane.

After drying overnight at 40° C. under vacuum, 71.35 grams (89.0% yield) of a white powder were recovered. The product was analyzed for % C, % H, % N, HPLC, proton and phosphorus NMR.

| | Analysis | | |
|---|---|---|---|
| | % C | % H | % N |
| Found | 62.08, 62.31 | 6.24, 6.23 | 3.56, 3.56 |
| Calculated | 64.68 | 5.92 | 3.77 |
| $1_H$ NMR(acetone-$d_6$) $\delta$6.9(phenyl s, 6H), $\delta$6.8-6.4(phenyl multiplet, 12H), $\delta$6.2(vinyl multiplet, 12H), $\delta$3.6(methyl s, 18H), $\delta$3.3(methylene, 8H), $\delta$1.8(methyl d, 18H). | | | |
| $^{31}$P NMR(acetone) $\delta$9.7(s). | | | |

B. Copolymerization of Hexakis(isoeugenoxy(cyclotriphosphazene and methylenedianiline bis-maleimide (X25890-75)

Hexakis(isoeugenoxy)cyclotriphosphazene (9.42 g, 0.0085 mol) and 1,1-methylene-4,1-phenylene)bis-maleimide (3.03 g, 0.0085 mol) were ground together and then heated to 170° C. under vacuum for two hours.

The temperature was then raised to 240° C. and held for two hours. A light brown polymer resulted.

Upon heating at 20° C. per minute, the residue at 900° C. was 26.49% in air and 40.25% in nitrogen. Onset of degradation occurred at about 385° C. in air and 410° C. in nitrogen.

What is claimed:

1. A crosslinked thermoset polymer which comprises a heat-catalyzed reaction product of a bis-maleimide based dienophile and an aryl or aryloxy substituted cyclophosphazene wherein an average of at least two aryl or aryloxy groups are substituted with an allyl or vinyl group.

2. A crosslinked thermoset polymer which comprises a heat-catalyzed reaction product of a bis-maleimide based dienophile and a cyclophosphazene having the general formula:

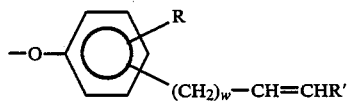

where n is 3 or 4 and $R_1$ and $R_2$ are the same of different and are selected from the group consisting of:

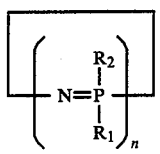
(a)

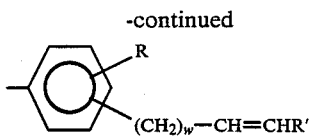
(b)

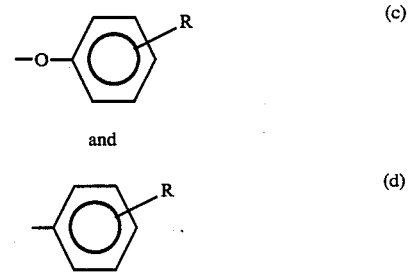
(c)

and (d)

where w=0 or 1, and R and R' are H or a nonreactive moiety, and the average degree of substitution per cyclophosphazene ring by $R_1$ and $R_2$ radicals selected from the group consisting of:

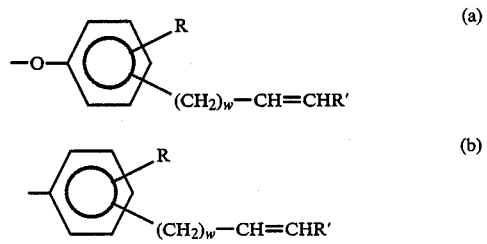
(a)

(b)

is at least two.

3. The polymer of claim 2 which is the reaction product of hexakis(isoeugenoxy) cyclotriphosphazene and methylenedianiline bis-maleimide.

4. The polymer of claim 2 which is the reaction product of tris(eugenoxy) tris(phenoxy) cyclotriphosphazene and methylenedianiline bis-maleimide.

* * * * *

UNITED STATES PATENT AND TRADEMARK OFFICE
CERTIFICATE OF CORRECTION

PATENT NO. : 4,874,828
DATED : October 17, 1989
INVENTOR(S) : Alexander Lukacs, III It is certified that error appears in the above-identified patent and that said Letters Patent is hereby corrected as shown below:

Column 1, line 7 between "which are" and "reaction" "superior" should be deleted.

Column 1, line 7 " proiducts "

should read -- products --

Column 1, line 22 " grouips "

should read -- groups --

Column 2, line 25 " cyclotriphosphazene "

should read -- cyclotetraphosphazene --

Signed and Sealed this

Thirtieth Day of October, 1990

Attest:

HARRY F. MANBECK, JR.

Attesting Officer  Commissioner of Patents and Trademarks